(12) United States Patent
Franz et al.

(10) Patent No.: US 9,365,593 B2
(45) Date of Patent: *Jun. 14, 2016

(54) PHOTOLABILE CAGED TRANSITION METAL COMPLEXES AND METHODS OF USING THE SAME

(71) Applicant: Duke University, Durham, NC (US)

(72) Inventors: Katherine J. Franz, Durham, NC (US); Katie L. Ciesienski, Chestnut Hill, MA (US)

(73) Assignee: Duke University, Durham, NC (US)

( * ) Notice: Subject to any disclaimer, the term of this patent is extended or adjusted under 35 U.S.C. 154(b) by 379 days.

This patent is subject to a terminal disclaimer.

(21) Appl. No.: 13/848,223

(22) Filed: Mar. 21, 2013

(65) Prior Publication Data

US 2013/0210793 A1     Aug. 15, 2013

Related U.S. Application Data

(63) Continuation of application No. 13/055,788, filed as application No. PCT/US2009/004278 on Jul. 23, 2009, now Pat. No. 8,440,827.

(60) Provisional application No. 61/085,146, filed on Jul. 31, 2008.

(51) Int. Cl.

| | | |
|---|---|---|
| *C07F 1/08* | (2006.01) | |
| *C07D 213/81* | (2006.01) | |
| *A61K 9/00* | (2006.01) | |
| *A61K 41/00* | (2006.01) | |
| *C07D 213/40* | (2006.01) | |
| *C07D 257/00* | (2006.01) | |
| *C07D 401/12* | (2006.01) | |
| *C07D 405/12* | (2006.01) | |

(52) U.S. Cl.
CPC .............. *C07F 1/08* (2013.01); *A61K 9/0024* (2013.01); *A61K 41/0042* (2013.01); *C07D 213/40* (2013.01); *C07D 213/81* (2013.01); *C07D 257/00* (2013.01); *C07D 401/12* (2013.01); *C07D 405/12* (2013.01)

(58) Field of Classification Search
CPC ...... A61K 41/0042; C07F 1/08; C07D 401/12
USPC ....................... 514/185, 188, 336; 546/6, 262
See application file for complete search history.

(56) References Cited

U.S. PATENT DOCUMENTS

| | | |
|---|---|---|
| 4,987,227 A | 1/1991 | Burrows et al. |
| 5,130,493 A | 7/1992 | Schnatterer et al. |
| 5,428,154 A | 6/1995 | Gansow et al. |

FOREIGN PATENT DOCUMENTS

WO     WO 2008/020920 A1     2/2008

OTHER PUBLICATIONS

Bednarski PJ et al. Photoactivatable platinum complexes. Anti-Cancer Agents in Medicinal Chemistry. 2007; 7: 75-93.
Ciesienski KL et al. A photolabile ligand for light-activated release of caged copper. J Am Chem Soc. Epub Aug. 21, 2008: 4 pp.
International Search Report, PCT/2009/004278, Dec. 23, 2009.

*Primary Examiner* — Barbara P Badio
*Assistant Examiner* — Sara E Townsley
(74) *Attorney, Agent, or Firm* — Myers Bigel Sibley & Sajovec, P.A.

(57) ABSTRACT

The present invention provides compounds of Formula I:

along with compositions comprising the same and methods of using the same, such as for photodynamic therapy in the treatment of cancer.

18 Claims, 1 Drawing Sheet

PHOTOLABILE CAGED TRANSITION METAL COMPLEXES AND METHODS OF USING THE SAME

RELATED APPLICATIONS

This application is a continuation of U.S. patent application Ser. No. 13/055,788, filed Mar. 15, 2011, now allowed, which in turn is a 35 U.S.C. §371 national phase entry of PCT Application PCT/US2009/004278, filed Jul. 23, 2009, and published in English on Feb. 4, 2010, as International Publication No. WO 2010/014179, and which claims the benefit under 35 U.S.C. §119(e) of U.S. Provisional Patent Application Ser. No. 61/085,146, filed Jul. 31, 2008, the disclosure of each of which is incorporated herein by reference in its entirety.

FIELD OF THE INVENTION

The present invention concerns transition metal compounds, compositions containing the same, and methods of using the same.

BACKGROUND OF THE INVENTION

The redox activity of copper makes it an essential cofactor in numerous enzymes critical for life, but also renders it potentially toxic by promoting the formation of reactive oxygen species (ROS) that lead to cellular oxidative stress.[1,2] Understanding the trafficking pathways by which cells and organisms acquire, maintain, and utilize copper while suppressing its toxicity has important ramifications for health and disease.[3,4] Copper's prooxidant property is also medicinally promising if it could be harnessed to induce oxidative stress as a cancer chemotherapy strategy.[5-7] New reagents that could deliver copper intracellularly in a site and time specific manner would therefore be useful both for targeted delivery of ROS-active agents and for delineating copper trafficking and utilization pathways.

SUMMARY OF THE INVENTION

A first aspect of the invention is a compound of Formula I:

(I)

wherein:

Z is a transition metal optionally having a coordinated water molecule, or Z is absent;

each X is independently selected from the group consisting of $NR^1$ and S, each of which can be substituted with with H if Z is absent;

each X' is independently selected from the group consisting of N, $NR^1$, and S;

each $R^1$ is independently selected from the group consisting of: H, alkyl, cycloalkylalkyl, heterocycloalkyl, arylalkyl, heteroarylalkyl, alkoxy, halo, formyl, hydroxyl, acyl, aryloxy, alkylthio, amino, alkylamino, arylalkylamino, disubstituted amino, acylamino, acyloxy, ester, amide, and carboxyalkyl;

or each adjacent pair of $R^1$ and $R^2$ can independently form a heterocycloalkyl or heteroaryl group with respective heteroatom X';

each $R^2$, $R^3$, $R^4$, $R^5$, $R^6$ and $R^7$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, carboxyalkyl, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

or $R^4$ and $R^5$ can together together form oxo;

or $R^6$ and $R^7$ can together form oxo;

each $R^8$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

m is from 0 to 4;

n is from 1 to 2; and p is from 1 to 3;

or a salt thereof.

A further aspect of the present invention is a composition comprising a compound or active compound as described herein in a pharmaceutically acceptable carrier.

A further aspect of the invention is the use of a compound as described herein for the preparation of a medicament for photodynamic therapy and/or for treating cancer.

A further aspect of the invention is a compound as described herein for photodynamic therapy and/or for treating cancer.

A still further aspect of the invention is a method of generating a free metal ion, comprising the steps of: providing a compound of claim as described herein, and then exposing said compound to light at a frequency and intensity effective to release said metal ion Z from said compound.

A further aspect of the invention is, in a method of treating a subject in need thereof (e.g., a subject afflicted with cancer) with photodynamic therapy (PDT) by administering said subject an active compound and illuminating an affected tissue or region (e.g., cancer tissue or tumor(s)) of said subject with light, the improvement comprising utilizing as said active compound a compound as described herein.

The foregoing and other objects and aspects of the present invention are explained in greater detail in the drawings herein and the specification set forth below.

DETAILED DESCRIPTION OF PREFERRED EMBODIMENTS

"Transition metal" as used herein refers to one of the 38 elements in groups 3 through 12 of the periodic table. In certain embodiments, the transition metals of this invention include, but are not limited to: scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, etc.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocycle-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise. "Heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, coumarin, isocoumarin, quinoline, isoquinoline, cinnoline, and the like. In some embodiments aryl contains a "hetero" atom and is also a "heterocyclo" group as described above. The term "aryl" is intended to include both substituted and unsubstituted aryl unless otherwise indicated and these groups may be substituted with the same groups as set forth in connection with alkyl and loweralkyl above. More specifically, "aryl" groups as used herein may be substituted 1, 2, 3, or 4 or more times with with independently selected halo (e.g., haloaryl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" or "carboxy" as used herein refers to a —C(O)OH group.

"Carboxyalkyl" as used herein refers to a carboxy group as defined herein, appended to the parent molecular moiety through an alkyl group as defined herein.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compounnd of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Treat" as used herein refers to any type of treatment that imparts a benefit to a patient afflicted with a disease or disorder, including improvement in the condition of the patient (e.g., in one or more symptoms), delay in the progression of the disease, etc.

"Cancer" as used herein may be any type of cancer, including but not limited to lung cancer, colon cancer, colorectal cancer, breast cancer, prostate cancer, ovarian cancer, liver cancer, leukemia, lymphoma, etc.

"Pharmaceutically acceptable" as used herein means that the compound or composition is suitable for administration to a subject to achieve the treatments described herein, without unduly deleterious side effects in light of the severity of the disease and necessity of the treatment.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

"Cells" as used herein with respect to in vitro cultures or compositions include plant, animal, and microbial cells, such as mammalian, avian, reptile, protozoal, fungal, yeast, gram negative bacterial, gram positive bacterial, monocot, and dicot cells, etc.

The disclosures of all United States patent references cited herein are to be incorporated by reference herein in their entirety.

1. Active Compounds.

As noted above, the present invention provides active compounds of Formula I:

wherein:

Z is a transition metal optionally having a coordinated water molecule, or Z is absent;

each X is independently selected from the group consisting of $NR^1$ and S, each of which can be substituted with with H if Z is absent;

each X' is independently selected from the group consisting of N, $NR^1$, and S;

each $R^1$ is independently selected from the group consisting of: H, alkyl, cycloalkylalkyl, heterocycloalkyl, arylalkyl, heteroarylalkyl, alkoxy, halo, formyl, hydroxyl, acyl, aryloxy, alkylthio, amino, alkylamino, arylalkylamino, disubstituted amino, acylamino, acyloxy, ester, amide, and carboxyalkyl;

or each adjacent pair of $R^1$ and $R^2$ can independently form a heterocycloalkyl or heteroaryl group with respective heteroatom X';

each $R^2$, $R^3$, $R^4$, $R^5$, $R^6$ and $R^7$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, carboxyalkyl; hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

or $R^4$ and $R^5$ can together together form oxo;

or $R^6$ and $R^7$ can together form oxo;

each $R^8$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

m is from 0 to 4;

n is from 1 to 2; and p is from 1 to 3;

or a salt thereof.

In some embodiments of the foregoing, Z is absent.

In some embodiments of the foregoing, Z is a transition metal (e.g., copper, platinum, iron or zinc).

In some embodiments of the foregoing, at least one adjacent pair (or both pairs) of $R^1$ and $R^2$ together form a heteroaryl (or heterocycloalkyl) (e.g., pyrimidine, thiazole, thiophene, isoquinoline, imidazole, or pyrroline).

In some embodiments of the foregoing, $R^7$ is H, alkyl, alkoxy, halo, or sulfonate.

In some embodiments of the foregoing, $R^6$ is H, alkyl, alkoxy, halo, or sulfonate.

In some embodiments of the foregoing, $R^5$ is H, alkyl, alkoxy, halo, or sulfonate.

In some embodiments of the foregoing, $R^4$ is H, alkyl, alkoxy, halo, or sulfonate.

In some embodiments of the foregoing, $R^4$ and $R^5$ together form oxo.

In some embodiments of the foregoing, each $R^3$ is independently H, alkyl, alkoxy, halo, or sulfonate.

In some embodiments of the foregoing, each $R^2$ is independently: H, alkyl, alkoxy, halo, or sulfonate.

In some embodiments of the foregoing, each $R^1$ is independently H, alkyl, alkoxy, or halo.

Particular examples of active compounds of the present invention include but are not limited to:

-continued

-continued where Z is a transition metal (optionally having water coordinated thereto) or is absent (in which case Z may represent a pair of hydrogen atoms, H,H).

In some embodiments the compound of Formula I is a compound of Formula Ia:

(Ia)

wherein m, n, X, X', Z, $R^1$, $R^2$, $R^3$, $R^4$, $R^5$, $R^6$, $R^7$, and $R^8$ are as given in connection with Formula I above. An example of a compound of Formula I is:

Additional examples of compounds of the present invention include the following:

-continued

-continued

The active compounds disclosed herein can, as noted above, be prepared in the form of their salts, including for some purposes pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Pharmaceutically acceptable prodrugs as used herein refers to those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/ dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art. As a general proposition, a dosage from about 0.1 or 1.0 to about 250 or 500 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 200 mg/kg may be employed for oral administration. Typically, a dosage from about 1 mg/kg to 100 mg/kg may be employed for intramuscular injection. The duration of the treatment is usually once per day for a period of two to three weeks or until the condition is essentially controlled. Lower doses given less frequently can be used prophylactically to prevent or reduce the incidence of recurrence of the disease.

4. Photodynamic Therapy.

Photodynamic therapy is a known technique in which an active compound is administered to a subject in need of treatment (e.g., due to cancer, a bacterial infection of an affected tissue or region, etc.) and then the affected region (e.g., a tumor, an inflammed region, etc.) is illuminated with light at the appropriate wavelength, intensity and duration to activate the active compound (in the case of the present invention, to cause release or "uncaging" of the metal ion) at the affected region. Numerous techniques and apparatus for carrying out photodynamic therapy are known, or will be apparent to those skilled in the art based on the present disclosure, and can be used in conjunction with the active agents described herein to carry out photodynamic therapy. See, e.g., U.S. Pat. Nos. 7,402,299; 7,390,668; 7,371,742; see also US Patent Application Publication No. 20060194960 to Kim and Lindsey.

5. In Vitro Use.

As noted above, the present invention provides a method of generating a free metal ion, comprising the steps of: providing a compound of claim as described herein, and then exposing said compound to light at a frequency and intensity effective to release said metal ion Z from said compound. While such generation can be carried out in vivo for the purposes discussed above, it can also be carried out in vitro, for diagnostic or research purposes (e.g., to examine the selective effect of the "caged" metal on a physiological system), e.g., by adding the compound to an in vitro composition, and the exposing step carried by simply illuminating the in vitro composition. Illumination can be with focused light, laser light, etc. The in vitro composition be a cell-free composition, or can comprise living cells.

The present invention is explained in greater detail in the following non-limiting Examples.

EXAMPLE 1

As one embodiment of the present invention, we present here a caged copper complex in which a photoactive nitrophenyl group is incorporated into the backbone of a tetradentate chelator with high affinity for copper. Activation with UV light induces bond cleavage that releases bidentate components with low affinity for copper (Scheme 1).

SCHEME 1

H₂cage
1

[Cu(OH₂)(cage)]
2 pic
3

4

The concept of light-activated caged metal ions was first introduced for $Ca^{2+}$.[8,9] Caged calcium, in which stable coordination complexes are activated by UV light to release $Ca^{2+}$ ions intracellularly, have found widespread use in understanding the many roles of $Ca^{2+}$ in neurotransmission, muscle contraction, and other biological processes.[10,11] The carboxylate-rich chelators used to cage $C^{a2+}$ have also been used for $Sr_{2+}$, $Ba^{2+}$, $Mg^{2+}$, $Cd^{2+}$, $Mn^{2+}$, and $Co^{2+}$,[12] while photocleavable cryptands have been reported to release alkali ions[13] and a photoactive crown ether shows modest reversible photorelease of $Sr^{2+}$.[14]

To the best of our knowledge, uncaging biologically important d-block metal ions like iron, zinc, and copper using photo-active ligands has not been reported. Because $Cu^{2+}$-carboxylate complexes are themselves photoactive to release $CO_2$ and carbon-centered radicals,[15] carboxylate ligands are not ideal for caging copper. We therefore chose a nitrogen-rich bispyridylamide ligand ($H_2$cage) for our first-generation caged copper.

A ligand $H_2$cage is obtained in a one-pot, two-step synthesis starting from 3-amino-3-(2-nitrophenyl)propionic acid. It is very soluble in methanol and ethanol and moderately soluble in water. Potentiometric titration of $H_2$cage shows that it contains no dissociable protons between pH 2 and 12, as expected since pKa values of substituted pyridines are below 2 and those of amide NH are above 12. In the presence of $Cu_{2+}$, however, protons are released from $H_2$cage at pH 3.3 and 4.8, consistent with deprotonation of both amides. Analysis of the pH-dependent spectrophotometric titration of a 1:1 mixture of H2cage and Cu2+ shows that the predominant species in solution from pH 5-12 is the neutral compound [Cu(OH₂)(cage)], with an overall stability constant of log ☐☐=10.8 (see experimental below). This value converts to a conditional dissociation constant, KD, at pH 7.4 for Cu-cage of 16 pM, which was further confirmed by a competition reaction between H2cage and the common chelator nitrilotriacetic acid (NTA), which has a KD of 23 pM for $Cu^{2+}$ at this pH (see experimental below).

Figure 1:
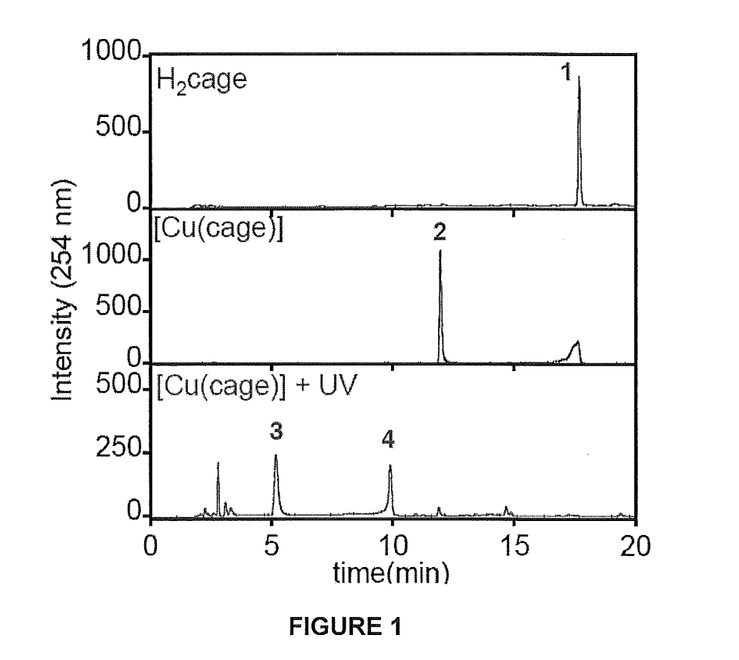
FIG. 1. Chromatography traces for H$_2$cage (top), [Cu(cage)] (middle), and [Cu(cage)] after 4 min of photolysis (bottom). Mass spectra corresponding to the LC peaks confirm the identity of ligand 1, copper complex 2, and photoproducts 3 and 4.

The affinity of our cage ligand for Cu2+ is slightly weaker than human serum albumin, the major copper-binding protein in blood, which binds $Cu^{2+}$ with 1 pM affinity at pH 7.4.16 Recrystallization of [Cu(OH$^2$)(cage)] from acetone in the presence of base confirmed that 2 deprotonated amide nitrogens and 2 pyridal nitrogens coordinate $Cu^{2+}$ in a distorted trigonal bipyramidal geometry, with a water molecule lying in the trigonal plane at a Cu—O distance of 2.299(3) Å. The average Cu—N amide distance of 1.943 Å and Cu—N pyridine distance of 2.034 Å are similar to other bispyridylamide $Cu^{2+}$ complexes.17-19 When solutions of [Cu(OH2)(cage)] in pH 7.4 phosphate buffer are exposed to 350 nm UV light, changes in its UV-vis spectrum are apparent within seconds (see experimental below). The shift in the d-d band centered at 580 nm indicates a reorganization of the coordination sphere upon photolysis. Cleavage of the ligand is complete within 4 min of photolysis, as confirmed by LC-MS analysis shown in FIG. 1. The band for the intact Cu complex 2 disappears and is replaced by bands corresponding to the expected photoproducts 3 and 4, as confirmed by their mass spectra and by comparison to a picolinamide standard for 3. The uncaged copper is likely bound to these photoproducts in solution, but with significantly diminished affinity compared to the intact ligand 1, as the log ☐☐values for picolinamide are only 2.87 and 5.40 for the 1:1 and 1:2 species. Reduction to Cu1+ is also possible as a result of photolysis, although it would likely reoxidize to Cu2+ under these experimental conditions.

Figure 2:
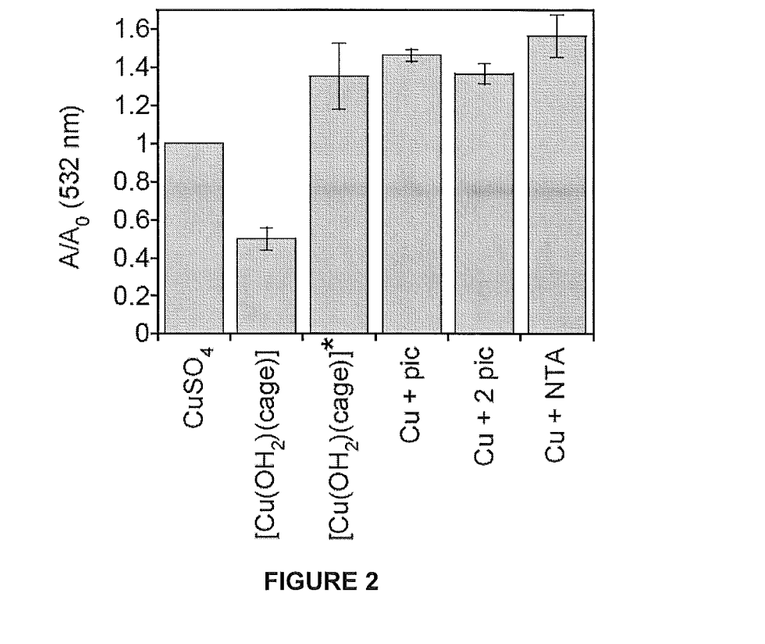
FIG. 2. Uncaging copper from [Cu(OH$_2$)(cage)] by UV photolysis increases OH. production as measured by the increase in A532 for deoxyribose degradation. A and A0 are the absorbance with and without ligand, so A/A0=1 for CuSO$_4$ alone; lower values indicate an inhibitory effect and higher values indicate a promotional effect of the ligand with respect to copper's reactivity for OH. production. [Cu(OH$_2$)(cage)] * was photolyzed for 4 min.

In order to show that photolysis of [Cu(OH$_2$)(cage)] causes a change in the reactivity of the caged vs. uncaged copper, we monitored the ability of the compounds pre- and post-photolysis to generate OH. radicals by subjecting them to the deoxyribose assay. Hydroxyl radicals, which are generated in this assay by Fenton-like conditions of copper, ascorbic acid, and H2O2, degrade deoxyribose to give thiobarbituric acid (TBA)-reactive products with absorbance at 532 nm. Ligands added to the reaction mixture attenuate the amount of TBA-reactive species by altering the coordination environment around copper. As shown in FIG. 2, our caging ligand provides 50% protection of deoxyribose degradation compared to the background reaction of $Cu^{2+}$ alone. The photo-products, on the other hand, increase the level of OH. produced. The reactivity of the photo-products matches that of control reactions run with 1 or 2 equiv of picolinamide, indicating that these bidentate ligands improve the catalytic properties of the metal with respect to Fenton-like chemistry. NTA, which has a similar affinity for $Cu^{2+}$ as H$_2$cage at this pH, also promotes OH. production by copper (FIG. 2).

This result highlights the fact that thermodynamic stability of a metal complex is not the fundamental factor dictating Fenton reactivity. Stability, redox potential, and the availability of reactive coordination sites all combine to modulate the reactivity of the metal center for oxidative reactions. This is a reverse strategy to our other efforts to develop chelating agents that can be triggered to inhibit oxidative stress.[20,21]

EXPERIMENTAL

Materials and Instrumentation. All chemicals were purchased commercially and used without further purification. N-Methylmorpholine (NMM), 2-deoxy-D-ribose, ascorbic acid, 50% hydrogen peroxide, trichloroacetic acid (TCA), and 2-thiobarbituric acid (TBA) were purchased from Acros Organics; picolinic acid, 2-(aminomethyl)pyridine, picolinamide, and CuSO$_4$.5H$_2$O from Sigma-Aldrich; nitrilotriacetic acid (NTA) from Fluka; 3-amino-3-(2-nitrophenyl)propionic acid from Alfa Aesar, and benzotriazol-yloxytris(dimethylamino) phosphoniumhexafluorophosphate (BOP) from Novabiochem. All solvents were reagent grade. Chromatographic purification was carried out on basic aluminum oxide (50-200 micron) from Acros Organics. $^1$H NMR and $^{13}$C NMR spectra were collected on a Varian Inova 400 spectrometer with chemical shifts reported in ppm and J values in Hz. Elemental analysis was performed by Columbia Analytical Services, Inc. IR spectra were measured on a Nicolet 380 FT-IR. High-resolution, fast-atom bombardment (HR-FABMS) mass spectra were recorded on JEOL JMS-SX-102 instrument. Liquid chromatography-electrospray mass spectrometry (LC/MS) was performed using an Agilent 1100 Series apparatus with an LC/MSD trap and a Daly conversion dynode detector. A Varian Polaris C18 (150×1.0 mm) column was used and peaks were detected by UV absorption at 254 nm. A linear gradient from 10% A in B to 60% A in B was run from 2 to 18 min with a total run time of 20 min, where A is MeCN/4% 10 mM ammonium acetate buffer and B is 10 mM ammonium acetate buffer/2% MeCN. UV-vis spectra were recorded on a Cary 50 UV-vis spectrophotometer. Photolysis experiments were performed using a screwtop quartz cuvette illuminated in a Rayonet RPR-100 Photochemical Reactor containing 16 bulbs, each 3500 Å.

Synthesis (1) Pyridine-2-carboxylic acid {1-(2-nitro-phenyl)-2-[(pyridine-2-ylmethyl)-carbamoyl]-ethyl}-amide (H$_2$cage). Equimolar quantities of picolinic acid (0.100 g, 0.813 mmol) and NMM (0.089 mL, 0.813 mmol) in CH$_2$Cl$_2$ (3 mL) were added to a 50-mL round-bottom flask equipped with a stir bar. The reaction mixture was cooled over an ice bath for ten min then BOP (0.360 g, 0.813 mmol) in CH$_2$Cl$_2$ (2 mL) was added. The reaction mixture was allowed to warm to room temperature with stirring for 18 h. After 18 h, one equivalent of 3-amino-3-(2-nitrophenyl)propionic acid (0.171 g, 0.813 mmol) dissolved in hot DMF (15 mL) was added and the reaction mixture was stirred for an additional 18 h. NMM (0.089 mL, 0.813 mmol) and 2-(aminomethyl)pyridine (0.083 mL, 0.813 mmol), both in CH$_2$Cl$_2$ (3 mL) were added to the reaction mixture. The resulting solution was cooled over an ice bath for ten min then BOP (0.360 g, 0.813 mmol) in CH$_2$Cl$_2$ (2 mL) was added, and the reaction mixture stirred for 18 h at room temperature. The solvent was removed and the resulting oil was taken up in CH$_2$Cl$_2$ (25 mL), filtered, and washed with saturated aqueous NaCl solution (3×10 mL). The organic layers were combined, dried over MgSO$_4$, filtered, and solvent removal gave an oil that was purified by chromatography (basic alumina, EtOAc:hexanes, 8:2, R$_f$=0.37), giving a white crystalline solid (0.220 g, 67%). $^1$H NMR (CD$_3$OD): δ 8.69 (1H, d, J=4.77), 8.42 (1H, d, J=4.93), 8.03 (2H, dd, J=4.65, J=7.97), 7.95 (1H, td, J=1.66, J=7.68, J=7.80), 7.74 (1H, d, J=6.77), 7.61 (3H, m), 7.53 (1H, dd, J=4.31, J=11.17), 7.25 (1H, m), 7.17 (1H, d, J=7.88), 6.08 (1H, dd, J=5.06, J=7.09), 4.47 (2H, dd, J=15.91, J=42.40), 3.11 (2H, qd, J=6.11, J=14.80, J=14.81, J=14.81). $^{13}$C NMR (CDCl$_3$): δ 40.5, 44.1, 47.6, 122.1, 122.2, 122.5, 124.9, 126.3, 128.3, 129.1, 133.6, 137.0, 137.2, 137.3, 148.2, 148.5, 148.6, 149.6, 155.8, 164.0, 170.4; HR-FABMS: m/z 406.11 [M+H]$^+$, M=C$_{21}$H$_{19}$N$_5$O$_4$; IR (MeOH, cm$^{-1}$): 3309, 1658, 1520, 1433, 1349, 731; UV-vis (H$_2$O, pH 6-12), nm (M$^{-1}$ cm$^{-1}$): 300 (1,800), 270 (8,500), 350 (410).

(2) [Cu(OH$_2$)(cage)]. A 50 mM aqueous solution of NaOH (9.38 mL) was added dropwise to a refluxing solution of H$_2$cage (0.095 g, 0.234 mmol) and CuSO$_4$.5H$_2$O (0.058 g, 0.234 mmol) in 25 mL of EtOH. After refluxing for 1 h, the solvent was removed and the residue was taken up in acetone and filtered. Slow evaporation gave blue, prism-shaped crystals in 81% yield. ESI-MS: m/z 467.0 [M+H]$^+$ for [Cu(cage)];

IR (neat, cm$^{-1}$): 1579, 1556, 1515, 1375, 1346, 1018, 755, 716, 698, 672, 647; UV-vis (H$_2$O, pH 6-12), nm (M$^{-1}$cm$^{-1}$): 580 (112); Anal. calcd. for C$_{21}$H$_{17}$CuN$_5$O$_4$.2H$_2$O: C, 50.15; H, 4.21; N, 13.92; found: C, 51.86; H, 4.25; N, 13.97%.

Deoxyribose Assay for Hydroxyl Radical Production. The 2-deoxyribose assay was used to measure hydroxyl radical formation (Halliwell, B.; Gutteridge, J. M. C.; Aruoma, O. I. *Anal. Biochem.* 1987, 165, 215-219). A mixture of copper, ascorbic acid, and hydrogen peroxide generates hydroxyl radicals by Fenton-like chemistry. Hydroxyl radicals attack 2-deoxyribose to form malondialdehyde (MDA), which upon heating with TBA under acidic conditions produces a pink chromophore ($\lambda_{max}$=532 nm). Chelators that prevent copper from reacting with ascorbic acid and hydrogen peroxide result in less chromophore formation. All assays were performed using 20 mM NaH$_2$PO$_4$ buffered to pH 7.4. The following reagents were added sequentially to obtain a 1 mL buffered solution with these final concentrations: chelator (10-20 µM), CuSO$_4$ (10 µM), 2-deoxyribose (15 mM), H$_2$O$_2$ (100 µM), and ascorbic acid (2 mM). For photolyzed samples, 500 µM solutions of [Cu(OH$_2$)(cage)] in 20 mM pH 7.4 NaH$_2$PO$_4$ buffer were photolyzed in screwtop quartz cuvettes for 4 min in the photoreactor, then immediately diluted into the deoxyribose reaction mixtures to obtain final concentrations of 10 µM in Cu. Stock solutions of CuSO$_4$, ascorbic acid, and H$_2$O$_2$ were prepared fresh daily, other solutions were prepared weekly. The reaction mixtures were stirred at 37° C. for 1 h, then 1 mL of TBA (1% w/v in 50 mM NaOH) and 1 mL of TCA (2.8% w/v in water) were added. The temperature was increased to 100° C. for 20 min, then cooled to room temperature and the absorbance at 532 nm was recorded. Values are reported as A/A$_0$ where A$_0$ is the absorbance without chelator present and A is the absorbance with chelator added. The value for CuSO$_4$ alone is A/A$_0$=1. Error bars represent standard deviations from measurements done in at least triplicate.

Potentiometric and Spectrophotometric Titrations. Cu(II) perchlorate solutions (0.1 M) were prepared from solid Cu(ClO$_4$)$_2$.6H$_2$O and standardized with 0.05 M EDTA to a murexide endpoint in ammonia buffer. NaOH, HClO$_4$, and NaClO$_4$ solutions (0.1 M) were prepared with boiled nanopure deionized water and were degassed upon cooling to remove dissolved carbonate. NaOH solutions were standardized by titration with both 0.2 M HCl and potassium hydrogen phthalate to a phenolphthalein end point and were stored under Ar; HClO$_4$ stock solutions were prepared from concentrated perchloric acid and standardized by titration with standard NaOH to a phenolphthalein end point. All solutions were degassed with Ar for 45 minutes prior to each experimental run.

Titrations were carried out at 25° C. with 0.1 M NaClO$_4$ supporting electrolyte in a 3-mL cuvette equipped with a pH probe, titrator tip, and stir bar, and blanketed in Ar to preserve an inert environment. The glass-bulb probe (Orion combination pH electrode model 8103BN filled with 3 M NaCl) was calibrated with pH 4 and 7 standard reference buffers (RICCA Chemical Company). CuL solutions were prepared by dissolving [Cu(OH$_2$)(cage)] recrystallized from methanol in 0.1 M NaClO$_4$ to obtain CuL concentrations in the range of 0.5 mM. Initial volumes were between 2 and 2.2 mL. A Schott TITRONIC® 110 plus autotitrator kept under constant Ar sparge was used to deliver 2 to 4 µL aliquots of acid or base through the titrator tip into the reaction cuvette. The solutions were stirred constantly and allowed to equilibrate at least 30 s after each addition before data were collected. All titrations were carried out from low to high and from high to low pH with similar results.

Titration data of the apo-ligand reveal no ionizable protons in the pH range between 2-12. This is not surprising, based on literature pK$_a$ values of amide protons (pK$_a$>20) and relevant substituted pyridine rings (pK$_a$<2).

Titration data for the CuL complex show two ionizable protons below pH 5. These data were fit using Specfit software (Spectrum Software Associates, version 3.0.30) according to the model in Table 1, where β is defined by Eq. 1 for the general equilibrium reaction in Eq. 2. The Specfit program produced log β values of 15.63 and 18.96 for the CuLH and CuLH$_2$ species respectively, which correspond to the pK$_a$ values of 4.83 and 3.33. Attempts to include the species CuLH$_{-1}$, which represents the deprotonation of the coordinated water molecule in [Cu(OH$_2$)(cage)], into the model did not fit the data, indicating that this event is not observable in the tested pH range (data not shown).

$$\beta_{mlh} = \frac{[Cu_mL_lH_h]}{[Cu]^m[L]^l[H]^h} \quad \text{Eq. 1}$$

$$m\text{Cu} + l\text{L} + h\text{H} \rightleftharpoons Cu_mL_lH_h \quad \text{Eq. 2}$$

TABLE 1

Model used for the pH-dependent spectrophotometric titrations of CuL, where L = cage$^{2-}$. β is defined in Eq. 1.

| Species | Log β | Cu m | L l | H h | |
|---|---|---|---|---|---|
| CuL | 10.80 ± 0.01 | 1 | 1 | 0 | Refined |
| CuLH | 15.63 ± 0.08 | 1 | 1 | 1 | Refined |
| CuLH$_2$ | 18.96 ± 0.03 | 1 | 1 | 2 | Refined |
| CuOH | −8.2 | 1 | 0 | −1 | Constant[ii] |
| Cu(OH)$_2$ | −17.5 | 1 | 0 | −2 | Constant[ii] |
| Cu(OH)$_3$ | −27.8 | 1 | 0 | −3 | Constant[ii] |
| Cu(OH)$_4$ | −39.1 | 1 | 0 | −4 | Constant[ii] |
| OH | −13.74 | 0 | 0 | −1 | Constant[iii] |

[i]Halliwell, B.; Gutteridge, J. M. C.; Aruoma, O. I. *Anal. Biochem.* 1987, 165, 215-219.
[ii]Kragten, J. *Atlas of Metal-Ligand Equilibria in Aqueous Solution*; Ellis Horwood: New York, 1978.
[iii]Martell, A. E.; Smith, R. M. In *NIST Standard Reference Database 46*; 6.0 ed.; Motekaitis, R. J.; NIST: Gaithersburg, MD, 2001.

Competition study of nitrilotriacetic acid (NTA) vs. cage for Cu$^{2+}$. Solutions of CuL (where L=cage$^{2-}$) were prepared by dissolving [Cu(OH$_2$)cage] that was recrystallized from methanol into 50 mM HEPES (N-(2-hydroxyethyl)-piperazine-N'-2-ethanesulfonic acid) buffer, pH 7.4, with initial concentrations ranging from 0.3-1.5 mM. The reaction vessel was a 3-mL cuvette and initial solution volumes were 1 mL. All titrations were carried out at 25° C. Aliquots (1-2 µL) of the competitive chelator NTA (100 mM) were pipetted into CuL solutions and monitored spectrophotometrically. After each addition, solutions were manually mixed and equilibrated for 5 min before data were collected. Data were fit to the model shown in Table 2 with Specfit software. Reported errors in log β were calculated from the standard deviation of three runs.

TABLE 2

Model for the Cu$^{2+}$ competition study of NTA vs. L, where L = cage$^{2-}$. β is defined in Eq. 1.

| Species | Log β | Cu m | NTA l | L l | H h | |
|---|---|---|---|---|---|---|
| CuL | 10.79 ± 0.06 | 1 | 0 | 1 | 0 | Refined |
| Cu(NTA) | 12.7 | 1 | 1 | 0 | 0 | Constant[iii] |
| Cu(NTA)$_2$ | 17.4 | 1 | 2 | 0 | 0 | Constant[iii] |

TABLE 2-continued

Model for the $Cu^{2+}$ competition study of NTA vs. L, where L = $cage^{2-}$. β is defined in Eq. 1.

| Species | Log β | Cu m | NTA l | L l | H h | |
|---|---|---|---|---|---|---|
| NTAH | 9.46 | 0 | 1 | 0 | 1 | Constant[iii] |
| NTAH$_2$ | 11.95 | 0 | 1 | 0 | 2 | Constant[i] |
| NTAH$_3$ | 13.76 | 0 | 1 | 0 | 3 | Constant[iii] |
| NTAH$_4$ | 14.76 | 0 | 1 | 0 | 4 | Constant[i] |
| CuOH | −8.2 | 1 | 0 | 0 | −1 | Constant[ii] |

[i]Halliwell, B.; Gutteridge, J. M. C.; Aruoma, O. I. *Anal. Biochem.* 1987, 165, 215-219.
[ii]Kragten, J. *Atlas of Metal-Ligand Equilibria in Aqueous Solution*; Ellis Horwood: New York, 1978.
[iii]Martell, A. E.; Smith, R. M. In *NIST Standard Reference Database* 46; 6.0 ed.; Motekaitis, R. J.; NIST: Gaithersburg, MD, 2001.

X-ray Data Collection and Structure Solution Refinement. Blue prisms of [Cu(OH$_2$)(cage)] were grown by slow evaporation of acetone. The crystal was mounted on the tip of a glass fiber and held in place by hardened Karo syrup. Data were collected at 296 K on a Bruker Kappa Apex II CCD diffractometer equipped with a graphite monochromator and a Mo Kα fine-focus sealed tube (λ=0.71073 Å) operated at 1.75 kW power (50 kV, 35 mA). The detector was placed at a distance of 5.010 cm from the crystal. A total of 2655 frames were collected with a scan width of 0.5° and an exposure time of 90.0 sec/frame. The frames were integrated with the Bruker SAINT v7.12A software package using a narrow-frame integration algorithm. Empirical absorption corrections were applied using SADABS v2.10 and the structure was checked for higher symmetry with PLATON v1.07. The structure was solved by direct methods with refinement by full-matrix least-squares based on $F^2$ using the Bruker SHELXTL Software Package. All non-hydrogen atoms were refined anisotropically. Hydrogen atoms of $sp^2$ hybridized carbons and nitrogens were located directly from the difference Fourier maps; all others were calculated. Table 3 contains a summary of crystal data, intensity collection and structure refinement parameters.

TABLE 3

Crystal data and structure refinement for [Cu(OH$_2$)(cage)].

| | |
|---|---|
| Identification code | md54 |
| Empirical formula | $C_{21}H_{19}N_5O_5Cu$ |
| Formula weight | 484.95 |
| Temperature | 296(2) K |
| Wavelength | 0.71073 Å |
| Crystal system | Monoclinic |
| Space group | P2(1)/n |
| Unit cell dimensions | a = 7.7037(4) Å  α = 90° |
| | b = 12.2546(8) Å  β = 95.364(3)° |
| | c = 21.0831(12) Å  γ = 90° |
| Volume | 1981.6(2) Å$^3$ |
| Z | 4 |
| Density (calculated) | 1.625 Mg/m$^3$ |
| Absorption coefficient | 1.149 mm$^{-1}$ |
| F(000) | 996 |
| Crystal size | 0.12 × 0.05 × 0.04 mm$^3$ |
| Crystal color and habit | Blue prism |
| Diffractometer | Bruker Kappa Apex II |
| Theta range for data collection | 1.92 to 24.96° |
| Limiting indices | −9 <= h <= 8, −14 < k <= 14, −25 <= l <= 25 |
| Reflections collected | 30154 |
| Independent reflections | 3429 [R(int) = 0.0815] |
| Completeness to theta = 24.96 | 98.9% |
| Absorption correction | Semi-empirical from equivalents |
| Max. and min. transmission | 0.9555 and 0.8744 |
| Solution method | SHELXS-97 (Sheldrick, 1990) |
| Refinement method | SHELXL-97 (Sheldrick, 1997) |
| Data/restraints/parameters | 3429/0/293 |
| Goodness-of-fit on $F^2$ | 1.152 |
| Final R indices [I > 2σ(I)] | R1 = 0.0410, wR2 = 0.0983 |
| R indices (all data) | R1 = 0.0664, wR2 = 0.1093 |
| Largest diff. peak and hole | 0.773 and −0.333e · Å$^{-3}$ |

REFERENCES (1) Peña, M. M. O.; Lee, J.; Thiele, D. J. *J. Nutrition* 1999, 1251-1260.

(2) Gaggelli, E. et al., *Chem. Rev.* 2006, 106, 1995-2044.

(3) Schlief, M. L.; Gitlin, J. D. *Mol. Neurobiol.* 2006, 33, 81-90.

(4) Madsen, E.; Gitlin, J. D. *Annu. Rev. Neurosci.* 2007, 30, 317-337.

(5) Wang, T.; Guo, Z. J. *Curr. Med. Chem.* 2006, 13, 525-537.

(6) Filomeni, G. et al., *J. Biol. Chem.* 2007, 282, 12010-12021.

(7) Farmer, P. J. et al., In *Medicinal Inorganic Chemistry*; Sessler, J. L. et al., Eds.; American Chemical Society: Washington, D.C., 2005; ACS Symposium Series 903, p 400-413.

(8) Kaplan, J. H.; Ellisdavies, G. C. R. *Proc. Natl. Acad. Sci. U.S.A.* 1988, 85, 6571-6575.

(9) Adams, S. et al., *J. Am. Chem. Soc.* 1988, 110, 3212-3220.

(10) Ellis-Davies, G. C. R. *Chem. Rev.* 2008.

(11) Adams, S. R.; Tsien, R. Y. *Ann. Rev. Physiol.* 1993, 55, 755-784.

(12) Kishimoto, T. et al., *J. Physiol.* 2001, 533, 627-637.

(13) Grell, E.; Warmuth, R. *Pure Appl. Chem.* 1993, 65, 373-379.

(14) Plaza, P. et al., *Chemphyschem* 2002, 3, 668-674.

(15) Sun, L.; Wu, C. H.; Faust, B. C. *J. Phys. Chem. A* 1998, 102, 8664-8672.

(16) Rozga, M. et al., *J. Biol. Inorg. Chem.* 2007, 12, 913-918.

(17) Stephens, F. S.; Vagg, R. S. *Inorg. Chim. Acta* 1984, 88, 7-14.

(18) Tsuboyama, S. et al., *Acta Crystallogr., Sect. B: Struct. Sci.* 1984, 40, 466-473.

(19) Comba, P.; Goll, W.; Nuber, B.; Varnagy, K. *Eur. J. Inorg. Chem.* 1998, 2041-2049.

(20) Charkoudian, L. K.; Pham, D. M.; Franz, K. J. *J. Am. Chem. Soc.* 2006, 128, 12424-12425.

(21) Charkoudian, L. K. et al., *Dalton Trans.* 2007, 43, 4873-5092.

The foregoing is illustrative of the present invention, and is not to be construed as limiting thereof. The invention is defined by the following claims, with equivalents of the claims to be included therein.

What is claimed is:

1. A compound of Formula I:

![Formula I structure]

wherein:
Z is a transition metal optionally having a coordinated water molecule, or Z is absent;
each X is independently selected from the group consisting of $NR^a$ and S, each of which can be substituted with H if Z is absent;
wherein $R^a$ is selected from the group consisting of: H, alkyl, cycloalkylalkyl, heterocycloalkyl, arylalkyl, heteroarylalkyl, alkoxy, halo, formyl, hydroxyl, acyl, aryloxy, alkylthio, amino, alkylamino, arylalkylamino, disubstituted amino, acylamino, acyloxy, ester, amide, and carboxyalkyl;
each X' is independently selected from the group consisting of N and S;
each adjacent pair of $R^1$ and $R^2$ independently form a heteroaryl group with respective heteroatom X';
each occurrence of $R^3$, $R^4$, $R^5$, $R^6$, and $R^7$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, aryl alkynyl, heteroaryl, heteroarylalkyl, heteroaryl alkenyl, heteroarylalkynyl, alkoxy, halo, mercapto, azido, cyano, formyl, carboxylic acid, carboxyalkyl, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;
or $R^4$ and $R^5$ can together together form oxo;
or $R^6$ and $R^7$ can together form oxo;
each $R^8$ is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;
m is from O to 4;
n is from 1 to 2; and
p is from 1 to 3;
provided that, when n is 1 or when p is 1, the corresponding $R^3$ is absent;
or a salt thereof.

2. The compound of claim 1, wherein Z is absent.

3. The compound of claim 1, wherein Z is a transition metal.

4. The compound of claim 1, wherein Z is a transition metal selected from the group consisting of copper, platinum, iron and zinc.

5. The compound of claim 1, wherein at least one adjacent pair of $R^1$ and $R^2$ together form a heteroaryl selected from the group consisting of pyrimidine, thiazole, thiophene, isoquinoline, imidazole, and pyrroline.

6. The compound of claim 1, wherein $R^7$ is selected from the group consisting of: H, alkyl, alkoxy, halo, and sulfonate.

7. The compound of claim 1, wherein $R^6$ is selected from the group consisting of: H, alkyl, alkoxy, halo, and sulfonate.

8. The compound of claim 1, wherein $R^5$ is selected from the group consisting of: H, alkyl, alkoxy, halo, and sulfonate.

9. The compound of claim 1, wherein $R^4$ is selected from the group consisting of: H, alkyl, alkoxy, halo, and sulfonate.

10. The compound of claim 1, wherein $R^4$ and $R^5$ together form oxo.

11. The compound of claim 1, wherein each $R^3$ is independently selected from the group consisting of: H, alkyl, alkoxy, halo, and sulfonate.

12. The compound of claim 1, wherein each $R^8$ is independently selected from the group consisting of: H, alkyl, alkoxy, and halo.

13. The compound of claim 1 having the structure:

![Compound structure]

or a salt thereof.

14. A composition comprising a compound of claim 1 in a pharmaceutically acceptable carrier.

15. A method of generating a free metal ion, comprising the steps of:
providing a compound of claim 1; and then
exposing said compound to light at a frequency and intensity effective to release said metal ion Z from said compound.

16. The method of claim 15, wherein said providing step comprises adding said compound to an in vitro composition and said exposing step comprises illuminating said in vitro composition.

17. The method of claim 16, wherein said in vitro composition comprises living cells.

18. The method of claim 17, wherein said in vitro composition is a cell-free composition.

* * * * *